United States Patent [19]
Brayer et al.

[11] Patent Number: 5,854,041
[45] Date of Patent: Dec. 29, 1998

[54] MYOGLOBIN WITH PEROXIDASE ACTIVITY

[75] Inventors: Gary D. Brayer, Richmond; Hung Lee, Guelph; A. Grant Mauk, Vancouver; Michael Smith, Vancouver; Harry Tong, Vancouver; Lianglu Wan, Vancouver, all of Canada

[73] Assignee: The University of British Columbia, Vancouver, Canada

[21] Appl. No.: 710,330

[22] Filed: Sep. 16, 1996

[51] Int. Cl.$^6$ ............................. C07K 14/805; C12N 9/08
[52] U.S. Cl. .............................................. 435/192; 530/385
[58] Field of Search ............................. 435/192; 530/385

[56] References Cited

PUBLICATIONS

Douglas, Don J. (Depart. of Chemistry, The University of British Columbia, Canada); Slides displayed at the following conferences and lectures: (a) The Asilomar Conference on Mass Spectrometry, Asilomar, California, USA; Sep. 25, 1995; (b) Battelle Pacific Northwest Labratories, Richland, Wash. USA; Oct. 1995; (c) Department of Medicinal Chemistry, University of Washington, Seattle, Wash.; Nov. 2, 1995; (d) The Lake Lousie Conference on Tandem Mass Spectrometry, Lake Louise, Alberta, Canada; Nov. 1995; (e) The 79th CSC Conference, St. John's, Newfoundland, Canada; Jun., 1996; and ASMS Conference on Mass Spectrometry and Allied Topics, Portland, Oregon, USA; May 12–16, 1996.

Guillemette et al., "Expression in *E. coli* of a Synthetic Gene Coding for Horse Heart Myoglobin" Protein Engineering 4: 585–592 (1991).

Hunter, C.L. et al., "Assessment of Hydrogen Bonding Contributions in a Gas Phase Protein by Mass Spectrometry" in: Proceedings of the 44th ASMS Conference on Mass Spectrometry and Allied Topics, Portland, Oregon 12–16 May, 1996 at p. 1093.

King, N.K. et al., "The Mechanism of Metmyoglobin Oxidation" The Journal of Biological Chemistry 238:1520–28 (1963).

Paice et al., "Bleaching Kraft Pulps With Oxidative Enzymes and Alkaline Ilydrogen Peroxide" TAPPI Journal 78:161–169 (1995).

Poulos, T.L. et al., "The Stereochemistry of Peroxidase Catalysis" The Journal of Biological Chemistry 255:8199–8205 (1980).

Rao, S.I. et al., "The Roles of His–64, Tyr–103, Tyr–146,and Tyr 151 in the Epoxidation of Styrene and β–Methylstyrene by Recombinant Sperm Whale Myoglobin" The Journal of Biological Chemistry 268:803–9 (1993).

Sundaramoorthy, M. et al., "The Crystal Structure of Manganese Peroxidase from *Phanerochaete chrysosporium* at 2.06–Å Resolution" The Journal of Biological Chemistry 269:32759–67 (1994).

Van Dyke, B.R. et al. "Site–directed Mutagenesis of Histidine Residues Involved in Cu (II) Binding and Reduction by Sperm Whale Myoglobin" Proc. Natl. Acad. Sci. USA 89:8016–19 (1992).

Wilks A. et al. "Intramolecular Translocation of the Protein Radical Formed in the Reaction of Recombinant Sperm Whale Myoglobin with $H_2O_2$" The Journal of Biological Chemistry 267:8827–33 (1992).

Zhang et al., "Oxidation of Residue 45 Mutant Forms of Pig DeoxyMB with $Fe(CN)_6^{3-4}$" Journal of Inorganic Biochemistry 48:79–84 (1992).

Stedman's Medical Dictionary, 26th ed., Williams & Wilkie, Baltimore, MD, p. 47, 1995.

Carlson et al., Biophysical J. 68(2 part 2):A87, 1995.

Carver et al., Biochemistry 30:4097–4705, 1991.

Balasubramanian et al., Biochemistry 32:2202–2212, 1993.

Lai et al., Proteins: Structure, Function and Genetics 22:322–339, 1995.

Huang et al., Structural Biol. 1:226–229, 1994.

Abadan et al., Biophys. J. 68:2497–2504, 1995.

*Primary Examiner*—Eric Grimes
*Attorney, Agent, or Firm*—Campbell & Flores LLP

[57] ABSTRACT

Myoglobin is shown to have Manganese ($Mn^{2+}$) binding and peroxidase capacity. Mn binding and peroxidase activity is enhanced by modification of the amino acid sequence of myoglobin to provide a Mn binding site on the surface of the protein near the heme group. Peroxidase activity of myoglobin not specific to Mn is enhanced by substituting amino acids at residues 39, 45, 46, 97 and 107 of myolglobin.

8 Claims, 4 Drawing Sheets

```
              1                   2                   3                   4                   5              6
              0                   0                   0                   0                   0              0
H   GLSDGEWQQVLNVWGKVEADTAGHGQEVLIRLFTGHPETLEKFDKFKHLKTEAEMKASED
W   VLSEGEWQLVLHVWAKVEADVAGHGQDILIRLFKSHPETLEKFDRFKHLKTEAEMKASED
B   GLSDGEWQAVLNAWGKVEADVAGHGQEVLIRLFTGHPETLEKFDKFKHLKTEAEMKASED
S   GLSDGEWQLVLNAWGKVEADVAGHGQEVLIRLFTGHPETLEKFDKFKHLKTEAEMKASED
h   GLSDGEWQLVLNVWGKVEADIPGHGQEVLIRLFKGHPETLEKFDKFKHLKSEDEMKASED 7                   8                   9                   1              1              1
              0                   0                   0                   0              1              0
                                                                          0              0
H   LKKHGTVVLTALGGILKKKGHHEAELKPLAQSHATKHKIPIKYLEFISDAIIH
W   LKKHGVTVLTALGAILKKKGHHEAELKPLAQSHATKHKIPIKYLEFISEAIIH
B   LKKHGNTVLTALGGILKKKGHHEAEVKHLAESHANKHKVPIKYLEFISDAIIH
S   LKKHGNTVLTALGGILKKKGHHEAEVKHLAESHANKHKIPVKYLEFISDAIIH
h   LKKHGATVLTALGGILKKKGHHEAEIKPLAQSHATKHKIPVKYLEFISECIIQ
```

FIGURE 1

○  ○ ○  ○  ▲                                                                                  ▼
1  GATCCATAACTAACTAATCTAGAAATAATTTTGTTTAACTTTAAGAAGGAGATATATCC
   GTATTGATTGATTAGATCTTTATTAAAACAAATTGAAATTCTTCCTCTATATAGG

10
   M   G   L   S   D   G   E   W   Q   Q   V   L   N   V   W   G   K   V   E   A
61 ATGGGTCTGTCTGATGGTGAATGGCAGCAGGTTCTGAACGTTTGGGGCAAAGTTGAAGCT
   TACCCAGACAGACTACCACTTACCGTCGTCCAAGACTTGCAAACCCCGTTTCAACTTCGA

30
   D   I   A   G   H   G   Q   E   V   L   I   R   L   F   T   G   H   P   E   T
121 GACATCGCTGGTCACGGTCAAGAAGTCTTGATTCGACTGTTCACCGGCCACCCGGAAACT
    CTGTAGCGACCAGTGCCAGTTCTTCAGAACTAAGCTGACAAGTGGCCGGTGGGCCTTTGA

```
        L  E  K  F  D  K  F  K  H  L  K  T  E  A  E  M  K  A  S  E
181  CTGGAAAAATTCGATAAATTCAAACACCTGAAAACTGAAGCTGAAATGAAGGCGTCTGAA
     GACCTTTTTAAGCTATTTAAGTTTGTGGACTTTTGACTTCGACTTTACTTCCGCAGACTT

D  L  K  K  H  G  T  V  V  L  T  A  L  G  G  I  L  K  K  K
241  GATCTGAAAAAACATGGTACCGTTGTGTTAACTGCCCTAGGTGGCATCCTTAAGAAAAAA
     CTAGACTTTTTTGTACCATGGCAACACAATTGACGGGATCCACCGTAGGAATTCTTTTTT

G  H  H  E  A  E  L  K  P  L  A  Q  S  H  A  T  K  H  K  I
301  GGGCACCACGAAGCTGAGCTCAAACCGCTTGCGCAATCGCATGCTACTAAACACAAGATC
     CCCGTGGTGCTTCGACTCGAGTTTGGCGAACGCGTTAGCGTACGATGATTTGTGTTCTAG
```

```
           110
     P I K Y L E F I S D A I H V L H S K H
361  CCGATCAAATACCTGGAATTCATCTCTGATGCGGATCATCCACGTTCTGCATTCTAAACAT
     GGCTAGTTTATGGACCTTAAGTAGAGACTACGCCTAGTAGGTGCAAGACGTAAGATTTGTA

130
     P G D F G A D A Q G A M T K A L E L F R
421  CCAGGTGACTTCGGTGCTGACGCTCAGGGTGCTATGACCAAAGCTCTCGAGCTGTTCCGT
     GGTCCACTGAAGCCACGACTGCGAGTCCCACGATACTGGTTTCGAGAGCTCGACAAGGCA

150
     N D I A A K Y K E L G F Q Q G □ □
481  AACGATATCGCTGCTAAGTACAAAGAACTGGGTTTCCAGGGTTAATGACTGCA
     TTGCTATAGCGACGATTCATGTTTCTTGACCCAAAGGTCCCAATTACTG
```

FIGURE 2C

MYOGLOBIN WITH PEROXIDASE ACTIVITY

BACKGROUND OF THE INVENTION

Peroxidase enzymes are heme containing proteins that catalyze oxidation of organic substances by peroxides. Peroxidase enzymes are known to be capable of catalysing the oxidization of phenolics in industrial processes. In the presence of hydrogen peroxide, the enzyme generates free radicals that link to form polymers. Generally, the reaction conditions require an enzyme that is active and stable at high temperatures (50°–60° C.), over a wide pH range (2 to 8), and in the presence of various solvents, peroxide inputs and sheer forces. Soybean peroxidase is known to be a suitable enzyme for use under such conditions.

Peroxidases are also used as an enzyme label for antigens, antibodies, oligonucleotide probes, and other biological reagents, for example in diagnostic kits and assays, tissue staining procedure and in related applications. Stability, activity and shelf life are desirable attributes of a peroxidase used in such applications.

Another use for peroxidase is in the treatment of waste streams, sludges, and soils contaminated with phenolics, aromatic amines, chlorinated organics, and/or heavy metals, where the enzyme could work with hydrogen peroxide to convert such compounds to less toxic or more easily removable high-molecular weight forms. Generally, the high cost, limited availability, and poor stability of peroxidase enzymes has precluded the practical use of such enzymes in waste biotreatment.

Manganese peroxidase (MnP) is one of the extracellular lignolytic heme enzymes produced by the while rot fungi *Phaneroceate chrysoporium* MnP catalyzes the oxidation of Mn(II) to Mn(III) by hydrogen peroxide by a mechanism that may be similar to that of horseradish peroxidase and cytochrome c peroxidase. By such a mechanism, reaction of the peroxidase Fe(III) heme iron with hydrogen peroxide would produce an oxidized form of the enzyme that possesses an Fe(IV)=0 center and a porphyrin-centered pi-cation radical center. This oxidized form of the enzyme oxidizes two equivalents of the Mn(II) substrate to regenerate the Fe(III) state of the enzyme. The Mn(III) produced by this reaction can function as a diffusible oxidizing species that can react with a variety of organic compounds including polymeric dyes and lignin model compounds and may be important in lignin degradation in nature. Manganese peroxidase from white rot fungi is known to be capable of degrading lignin in kraft pulp that is used for production of paper (Paice, M. G., et al. "Bleaching Kraft Pulps With Oxidative Enzymes and Alkaline Hydrogen Peroxide" (1995) *TAPPI Journal* 78: 161–169). However, the thermal stability of manganese peroxidase is not high having a typical melting temperature of 50° C.

Myoglobin (Mb) is a small heme containing protein that is capable of binding oxygen and is found in muscle cells. The protein is well characterized, having 153 amino acid residues of known sequence. Mb is relatively heat stable, exhibiting a typical melting point of approximately 76° C. Mb is very suitable for large scale production by recombinant means well known in the art.

When the iron atom in Mb is reduced to Fe(II), it can bind oxygen present in blood or in the atmosphere to form the oxyMb derivative. OxyMb will spontaneously oxidize to metMb in which the oxygen is no longer bound to the heme iron and the iron has changed to the Fe(III) state. After purification, Mb is in the Fe(III) state (metMb). In this form, the iron is bound by six atoms. Four of these atoms are nitrogen atoms that are provided by the planar heme prosthetic group. A fifth nitrogen atom is provided by the so-called "proximal" histidine residue (residue His92) that binds on the side of the heme plane that is opposite the site where oxygen blinds. The side of the heme where ligand binding occurs is referred to as the "distal" side of the heme. The sixth ligand is provided by a water molecule or a hydroxide group, depending on the pH.

Mb is also known to have peroxidase activity on organic substrates. Typically, when Mb is used to catalyse a peroxidase reaction, a solution is provided containing a substrate that will be oxidized during the reaction. The reaction is initiated by addition of a hydrogen peroxide ($H_2O_2$) solution. The sequence of events following addition of the peroxide is generally believed to follow the following course:

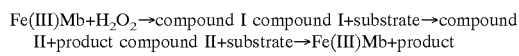

Fe(III)Mb+$H_2O_2$→compound I compound I+substrate→compound II+product compound II+substrate→Fe(III)Mb+product The term "compound I" refers to a transient intermediate form of Mb in which the Fe(III) has been oxidized by one equivalent to a ferryl group (Fe(IV)=0; the water molecule bound as the sixth ligand in metMb is deprotonated in this reaction to produce the oxygen ligand and a second group of the protein has been oxidized to a radical centre). The location of this radical site is not known but may involve one or more tyrosine residues. Compound I may not consist of a single chemical entity and may be a mixture of closely related derivatives.

Compound I is reduced by one equivalent by a molecule of substrate to produce a second intermediate, compound II. Compound II retains the Fe(IV)=0 iron centre that can be reduced by a second molecule of substrate. After this cycle, the original form of metMb (Fe(IIII)Mb) is regenerated and the process can start again as expected for a catalytic process.

SUMMARY OF THE INVENTION

This invention provides modified myoglobin having an amino acid sequence in which one or more of the following amino acid residues are substituted: Thr 39, Lys/Arg 45, Phe 46, Lys 63, His 97, and Ile 107, with the proviso that if only Lys/Arg 45 is substituted, it is not substituted with His, Ser, Glu, Arg, or Lys.

This invention also provides a method of catalysing a reaction with myoglobin in which a substrate is oxidized with a peroxide wherein, a reaction mixture is provided comprising substrate, peroxide and myoglobin, characterized in that the myoglobin has a modified amino acid sequence in which one or more of the following amino acids are substituted: Thr 39, Lys/Arg45, Phe/16, His 97 and Ile 107. The substrate may be Mn(II), This invention also provides a method of catalysing oxidation of Mn(II) by hydrogen peroxide with an enzyme, wherein a reaction mixture is provided comprising Mn(II) substrate, hydrogen peroxide and an enzyme catalyst, characterized in that the enzyme catalyst is myoglobin. The myoglobin may be wild-type or modified as described above and additionally by substitution at Lys63.

Although Mb is known to exhibit peroxidase activity, the ability of Mb to bind Mn or to use Mn(II) as a substate in this activity was not previously known. The present invention provides Mn(II) peroxidase activity of Mb and the enhancement of such activity by the modification of Mb through the introduction of a metal binding site on the surface of the protein at the edge of the heme prosthetic group that is partially exposed to solvent. This invention also provides modified Mb wherein peroxidase activity of the enzyme is enhanced which is not specific to Mn.

Throughout this specification, any reference to Mb is a reference to myoglobin regardless of source. The amino acid sequence of Mb is highly conserved among the species from which Mb has been characterized. Reference to a particular amino acid residue will be by the number of the residue from the amino-terminal end of the protein. A reference to a residue number preceeded by a single or three letter code for an amino acid will refer to the amino acid found at that site in a wild-type Mb. A reference to an amino residue number followed by a single or three letter amino acid code will refer to a particular amino acid that has been substituted at that site for the wild type amino acid. For example, reference to Lys/Arg 45 Glu or K/R45E refers to the substitution of the wild type lysine or arginine at residue number 45 with glutamic acid. The wild-type amino acids that are known to be present at residue 45 are lysine and arginine.

Mb may be prepared by chemical synthesis or recombinant techniques known in the art. Native Mb may be purified from a variety of natural sources and may be obtained commercially. Modified Mb in which native amino acids have been deleted or substituted with one or more amino acids may be prepared by techniques known in the art including chemical synthesis or by recombinant techniques whereby a sequence coding for the modified protein is expressed. Mutant Mb coding sequences may be obtained by various methods, including constructing such a sequence from synthesized oligonucleotides, or by mutation of a wild type or synthetic Mb gene through random or site directed mutagenesis.

Mb, including Mb modified according to this invention, may be used in a peroxidase reaction as described above, wherein the enzyme, substrate and a peroxide are provided in a reaction mixture. Where the reaction involves oxidation of Mn(II), the substrate will comprise the latter divalent metal ion and the reaction mixture may also include a metal chelator to facilitate dissociation of Mn(II) from Mb or stabilization of Mn(III) in solution. Suitable organic chelators include small organic diacids such as malonate.

BRIEF DESCRIPTION OF THE DRAWINGS

For better understanding of the invention, reference may be made to the preferred embodiments and examples described below, and the accompanying drawings, in which:

FIG. 1: shows the first 113 amino acid residues of five representative wild-type Mb proteins from horse hear (H) (SEQ ID NO: 1); sperm whale (S)(SEQ ID NO: 2); bovine (B)(SEQ ID NO: 3); sheep (S)(SEQ ID NO: 4); and human (H)(SEQ ID NO: 5).

FIG. 2: shows the DNA sequence (SEQ ID NO: 6) of a synthetic horse heart Mb gene derived from the illustrated Mb amino acid sequence (SEQ ID NO: 11) and employing codons preferred for expression in E. coli Upstream (°) and downstream (□) translational stop codons are shown. The sequence shown between symbols ▶ and ◀ is a XbaI—NcoI gene 10—leader sequence which includes a ribosomal binding site.

DESCRIPTION OF THE PREFERRED EMBODIMENTS

Modified Mb having enhanced peroxidase activity may have a substitution at residue 45. The following residue 45 mutant forms of pig myoglobin are already known: K45H, K45S, K45E, and K45R, but not the peroxidase activity of such mutants (Zhang, B-J et al. (1992) "Oxidation of Residue 45 Mutant Forms of Pig DeoxyMb with $[Fe(CN)_6]^{3-4}$"; Journal of Inorganic Biochemistry, 48: 79–84).

Preferably, modified Mb having enhanced peroxidase activity, in addition to optional substitution at residue 45, will be substituted at one or more residues 39, 46 and 107.

The modified Mb proteins described above exhibit enhanced peroxidase activity in general and may exhibit enhanced Mn(II) peroxidase activity as well, due in part to enhanced rate of reaction of Fe(III) Mb with hydrogen peroxide, and because the substitution at residue 45 creates a new Mn binding site which is stronger than the natural Mn binding site of Mb. The engineered Mn binding site is near the heme and better facilitates transfer of an electron to the oxidized centres of compounds I and II (as above). For Mn binding, it is preferable that an additional substitution be made at residue 63. Alteration of Mb sequence at other sites in combination with the aforementioned mutations may be made without loss of peroxidase or Mn binding activity. Substitutions at the aforementioned sites may be as described below.

Residues 39, 46, 97 and 107 may independently be replaced with any naturally occuring amino acid other than the amino acid found at each site. Preferably, the replacement amino acid at each site will be aliphatic, including: Leu, Ile, Val, Ala, Met, Phe, and Gly. Most preferably, the substitutions will be as follows Thr 39 Ilc, Phe 46 Leu, His 97 Leu and Ile 107 Phe.

Residue 45 may be replaced with any of the naturally occuring amino acids other than Lys or Arg which are found at that site in wild type Mb. Preferably, the replacement amino acid will be Trp or Cys. More preferably, and particularly for enhanced Mn binding, the replacement amino acid will be negatively charged, including Asp and Glu. A preferred mutant in combination with those described above is: Thr39Ilc, Lys/Arg 45 Glu, Phe 46 Leu, and Ile 107 Phe.

Residue 63 may be replaced with any naturally occuring amino acid but preferably not Arg, Trp or Cys. More preferably, the replacement will be aliphatic (preferably Ser or Thr), His, or negatively charged (preferably Asp or Glu). Most preferably the replacement is Asp or Glu and a preferred mutant in combination with those described above is: Thr 39 Ile, Lys/Arg 45 Asp, Phe 46 Leu, Lys 63 Glu, and Ilc 107 Phe.

EXAMPLE 1

Wild type Mb is now shown to have Mn(II) peroxidase activity by the following example in which the peroxidase reaction employs Mn(II) at substrate and is carried out in the presence of malonate. This reaction provides a useful assay for Mn(II) peroxidase activity since the rate of formation of Mn(III)-malonate complex may be monitored at 270 nm. This reaction, employing maganese peroxidase rather than Mb as enzyme, was described by Wariishi, J. et al. (1992) J. Biol. Chem. 267: 23688–23695.

The measurements are performed on a Cary-219 UV-visible spectrophotomerter equipped with a thermostatted cuvette holder and a Lauda Model RC-3 circulating water bath. The spectrophotomer is interfaced to a microcomputer and the data collected using OLIS software (Bogart, GA). The initial rate of reaction (units/$\mu$mol) are determined for each Mb variant under identical conditions (10 mM $MnSO_4$, 0.1 mM$H_2O_2$, 0.2 $\mu$M Mb) in 0.1 malonate buffer, pH 6.2 at 25° C. A unit of activity is defined as that amount causing a rate increase in absorbance at 270 nm of 1 per minute. Following this procedure the inventors have determined the commercially available (SIGMA) wild-type Mb has Mn(II) peroxidase activity. Wild-type horse heart Mb Mn(II) peroxidase activity is shown in Table 1.

TABLE 1

| Protein | Rate of Mn(II) turnover (units/μmol) |
| --- | --- |
| wild-type Mb | 14 ± 2 |
| K45E | 44 ± 7 |
| K45E/K63E | 51 ± 8 |
| U97L/K45E/K63E | 97 ± 5 |
| KH97L/K45E/K63E/S92A | 77 ± 5 |

EXAMPLE 2

Random mutagenesis of the synthetic Mb gene shown in FIG. 2 may be carried out to produce Mb variants. A standard PCR protocol is used (Leung, D. W. et al. (1989) "A method for Random Mutagenesis of A Defined DNA Segment Using A Modified Polymerase Chain Reaction", Technique 1:11–15), optimized to achieve only one amino acid replacement within Horse heart myoglobin: a 100 μl, reaction mixture contained 67 mM Tris-Cl, pH 8.8, 16.6 mM $(NH_4)_2SO_4$, 0.07% β-mercaptoethanol (V/V), 0.06 mM $MnSO_4$, 200 μM each of dNTP, 0.1 μM each of primers, 10 ng template DNA, 2.5 units Taq DNA polymerase (Life technologies) pGYM is used as the template for the first round of PCR random mutagensis. The successive rounds of PCR random mutagenesis use sequentially selected variant plasmid DNA as templates. The forward primer is −21M13 (5'-TGT AAA ACG ACG GCC AGT-3')(SEQ ID NO:7) and the reverse primer is M13R (5'-CAG GAA ACA GCT ATG ACC-3') (SEQ ID NO:8). PCR was carried out on a DNA thermal cycler (Perkin-Elmer Cetus) using step cycle: 96° C., 15 sec; 42° C., 30 sec; 72° C., 45 sec; 25 cycles; then 72° C., 10 min. The PCR reaction was checked by agarose gel electrophoresis and the amplified DNA fragments were purified using Wizard PCR Prep kit (Promega). The fragments and pGYM were digested separately with Pst I and Neo I, gel purified with Sephaglas BandPrep kit (Pharmacia) and ligated. The ligated plasmid was used to transform E. coli strain LE392 by either electroporation using Gene Pulser (BIO-RAD) or calcium chloride method (Cohen et al., (1972) Proc. Natl. Acad. Sci., 69: 2110). Throughout this specification the plasmid resulting from insertion of Mb gene shown in FIG. 2 (wild type or mutated) into the multiple cloning site of pEMBL18+ phagemid vector behind a lac promoter will be referred to as pGYM.

The transformed E. coli colonies are lysed on plates with chloroform and the mutants are screened for increased peroxidase activity by spraying the plates with 25 mM ABTS [2,2'-azino-di-(3-ethyl-benzthiazoline-6-sulphonic acid)] and 12.5 mM $H_2O_2$ in 0.1M potassium phosphate, pH 6.0. Colonies showing green color reaction from the original plates are used for plasmid mini-prep and subsequent transformation. The substrate concentration used in the screening procedures was described in order to select for mutants with greater peroxidase activities. The procedure of random mutagenesis described above was repeated in four sequential rounds of random mutagenesis and selection and a series of variants containing single, double, triple and quadruple substitutions with incrementally increased peroxidase activity were selected.

EXAMPLE 3

Mb variants as described in the preceding example were evaluated for peroxidase activity and other characteristics, as compared to wild-type horse heart Mb.

a) Purification of Recombinant Mb

A small inoculum of E. coli LE392 containing pGYM is grown at 37° C. overnight in Superbroth. The overnight culture is used to inoculate 30 ml (1:100 v/v) of Superbroth medium (tryptone (10 g/L), yeast extract (8 g/L). NaCl (5 g/L) and ampicillin (100 μg/L)) which is then incubated for 6 hours at 37° C. The mid-log phase culture is again used to inoculate (1:100 , v/v) 600 ml of Superbroth in a 2L flask followed by a 20th incubation at 37° C. The dark red cells are harvested and washed with NET buffer (100 mM NaCl, 1 mM EDTA, 50 mM Tris-HCl, pH 8.0) before storage at −70° C.

All the following steps are performed at 4° C. The frozen cells from 12L of bacterial culture are left overnight at 4° C. to thaw. Deoxyribonuclease 1 (10 mg. Sigma product D5025), ribonuclease A (1 mg; Sigma product R4875) and 20 ml of 2M $MgCl_2$ solution are added to the thawed cells, and the suspension is placed on ice for 2 hours. The resulting cellular debris is removed by centrifugation (in a Sorvall GS-3 rotor, 8000 rpm, 30 min) and washed once with buffer (20 mM Tris-HCl buffer, pH 8.0). The red supernatant solution is slowly brought to 55% saturation with solid ammonium sulfate and the proteins precipitated for 3 hours on ice. After centrifugation (as above), the supernatant liquid is filtered and then slowly brought to 100% saturation with solid ammonium sulfate. The solution is stored on ice overnight. The precipitate is collected by centrifugation, the pellet is resuspended in a minimal volume of ice cold water, and dialysed against 5 mM Tris-HCl, pH 8.4, 1 mM EDTA. The dialysed supernatant fluid is adjusted to pH 8.0 with 1.0M NaOH and centrifuged to remove any percipitate that may have formed during dialysis.

The crude Mb extract is loaded onto a column of DEAR Sepharose CL6 Hr (Pharmacia)(3×15 cm) equilibrated in 20 mM Tris/HCl pH 8.0. Myoglobin does not bind to this resin under these conditions, so fractions eluting directly from the column are loaded onto a column of Chelating Sepharose Fast Flow (Pharmacia)(3×10 cm) prepared by sequentially washing with water (300 ml), 50 mM ethylenediaminetetraacetic acid (300 ml), a solution of 35 mM $ZnSO_4$ that contained 25 mM acetic acid (300 ml), and buffer (20 mM Tris/HCl, 0.5M NaCl, pH 8.0) (300 ml). After binding Mb to this column, it is washed with 20 mM Tris/HCl (0.5M NaCl, pH 8.0) (200 ml) before developing with 20 mM Tris/HCl (0.5M, NaCl, 50 mM imidazole pH 8.0)(100 ml). The partially purified Mb is then concentrated by centrifugal ultrafiltration (Centriprep-10, Amicon) to a volume of ~15 ml and loaded onto a column of Sephadex G50 (Pharmacia) equilibrated and eluted with 20 mM Tris/HCl containing 1 mM ethylenediaminetetracetate (EDTA)(pH 8.0) for further purification. Myoglobin fractions (A408/A28≧3.5) are pooled and exchanged into 20 mM ethanolamine (pH 9.0). Final purification of the Mb may be achieved by optional elution over an 11R10/10 Mono-Q anion exchange column (Pharmacia) that is initially equilibrated with 20 mM ethanolamine pH 9.0 and developed with a linear gradient of NaCl (0–0.06M). The final product (A408/A280≦3.5) migrates as a single band by SDS-PAGE gel electrophoresis.

b) Steady-state kinetic assays

The steady-state kinetics of the peroxidase activity of wild-type and modified forms of horse heart myoglobin are determined by monitoring the oxidation of ABTS (2,2'-azido-di(3-ethyl)benzthiazol-indolsulfonate diammonium salt) by peroxidase at 414 nm (25° C., 0.1M MES buffer, pH 6.0). The reaction mixture contains myoglobin ($0.2 \times 10^{-6}$M), ABTS ($20 \times 10^{-6}$M) and varying concentrations of hydrogen peroxide in a final volume of 1 ml. Rates are measured by $\Delta A$ over 20 seconds at 25° C. on a Cary 1E UV-visible spectrophotometer. The rate data is analyzed in terms of the peroxidase ping-pong mechanism described by Dunford, H. B. In *Peroxidases in Chemistry and Biology*, J. Everse et al. Eds. (1991), Vol. II, CRC Press: Boca Raton, at p. 1–24. The mechanism involves the following reactions:

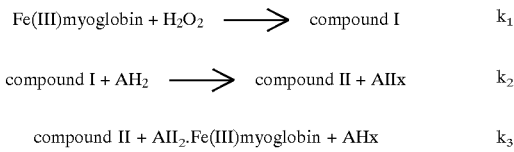

$$\text{Fe(III)myoglobin} + H_2O_2 \longrightarrow \text{compound I} \quad k_1$$

$$\text{compound I} + AH_2 \longrightarrow \text{compound II} + AH_x \quad k_2$$

$$\text{compound II} + AH_2.\text{Fe(III)myoglobin} + AH_x \quad k_3$$

For this mechanism, $2 [Mb_o]/V = 1/k_{1[H2O2]} + 1/k_{3[ABTS]}$, and $AH_2$ represents the substrate (ABTS). The results of this analysis can be seen in Table 2.

TABLE 2

| Protein | $k_1 (M^{-1}s^{-1})$ | Relative $k_1$ | $k_3 (M^{-1}s^{-1})$ | relative $k_3$ |
|---|---|---|---|---|
| wild-type Mb | $8.8 \times 10^3$ | 1 | $8.8 \times 10^5$ | 1 |
| T39I | $4.4 \times 10^4$ | 5.0 | $9.1 \times 10^5$ | 1.0 |
| F46L | $4.8 \times 10^4$ | 5.4 | $2.0 \times 10^6$ | 2.3 |
| I107F | $4.8 \times 10^4$ | 5.4 | $7.9 \times 10^5$ | 0.9 |
| F46L/I107F | $5.4 \times 10^4$ | 6.1 | $1.3 \times 10^6$ | 1.5 |
| T39I/F46L/I107F | $3.2 \times 10^5$ | 36.4 | $4.7 \times 10^6$ | 5.3 |
| T39I/K45D/F46L/I107F | $7.2 \times 10^5$ | 81.8 | $2.8 \times 10^6$ | 3.2 |

C) Thermal stability measurements

The stability of wild-type and variant forms of horse heart myoglobin are evaluated to determine their stability against thermal denaturation by monitoring the ellipticity of protein solutions at 222 nm as monitored with a spectropolarimeter. Myoglobin samples are placed in a temperature-controlled quartz cell and the temperatures is increased at a constant rate (slope) under computer control and the temperature at which half of the protein is denatured ($T_m$) was determined. The $T_m$(°C.) values for the following Mb variants are: F46L-76.1° C.; F46L/H07F-76.4° C.; T39I/F46L/I107F-76.2° C.: and T39I/K45D/F46L/I107F.-74.1° C.

Flash photolysis may be used to measure oxygen and carbon monoxide association rates. Gas binding parameters for the single—quadruple mutant Mb variants described above show increased peroxidase activity is achieved without significantly altering the oxygen carrying capacity or carbon monoxide binding of the Mb, with the exception of F46L in which the oxygen dissociation rate is significantly increased.

EXAMPLE 4

Site directed mutagenesis procedures which are known in the art may be used to produce the previously described Mb variants (eg. See J. J. Zoller and M. Smith (1987) "Oligonucleotide Directed Mutagenesis: A Simple Method Using Two Oligonucleotide Primers and a Single-Stranded DNA Template", Meth. Enzymol. 154:329–350; T. A. Kunkel (1985) "Rapid and Efficient Site-Specific Mutagenesis Without Phenotypic Selection" Proc. Natl. Acad. Sci. USA 82:488–492; and, Guillemette, J. G., et al. (1991) "Expression in *E. coli* of a Synthetic Gene Coding For Horse Heart Myoglobin", Protein Engineering 4:585–592.)

The following protocol for site directed mutagenesis, used here to create a new Mn(II) binding site in horse heart Mb, may be used to produce the specific site mutations disclosed in the preceding examples. Suitable oligodeoxyribonucleotides, derived from the DNA sequence shown in FIG. 2 will introduce appropriate mutant codons into the gene for ultimate expression of the desired Mb variant. The gene shown in FIG. 2 as well as suitable bacterial expression systems are described in Guillemette, J. G. et al. [supra].

In this example, mutagenic oligodeoxyribonucleotides are synthesized with a modified Applied Biosystems 380A DNA Synthesizer and purified with a Millipore C18 Sep Pak column. Single-stranded DNA for the mutagenesis template is prepared from the *E. coli* strain RZ1032 which is deficient in dUTPase and uracil-N-glycosylase (during). The resulting ssDNA, template contains a proportion of uridine instead of thymidine residues. When this wild-type template is subsequently transformed into *E. coli* strain JM101 (dut+ung+) after the mutagenic reaction, it has a selective disadvantage compared to the mutagenic strand of the DNA duplex.

In preparing single-stranded DNA template, pGYM vector containing the wild type Mb gene shown in FIG. 2 is transformed into competent *E. coli* RZ1032 cells using calcium chloride, for example by using the method of M. J. Zoller and M. Smith [supra]. A 1.5 ml. culture of freshly transformed cells is grown at 37° C. for 2–3 hours in LB broth (10 g/l. tryptone, 5 g/L, yeast extract, 10 g/L NaCl, 100 mg/L. ampicillin), then superinfected with a strain of phage R408 (2 μL of ~$10^{11}$ pfu/mL). and incubated for a further 6 hours. Cells are removed by centifugation, and the released phage is precipitated from the media by incubating in 0.2 volumes of 20% PEG 8000/3.5M ammonium acetate for 15 mins at room temperature. Phage particles are collected by centrifugation, resuspended in 100 μl. TE buffer (10 mM Tris-HCl, pH 8.0, 1 mM EDTA), and extracted with equal volumes of phenol, phenol/chloroform, and chloroform. Chloroform solution consisted of chloroform and isoamyl alcohol in a ratio of 24:1 DNA is recovered from the aqueous phase by ethanol precipitation (2.5 volumes of ethanol and 0.1 vol of 3M sodium acetate). Single-stranded DNA is then resuspended in 30 μL of TE buffer.

The complementary phosphorylated mutagenic oligonucletides (see Table 3, in which the mutagenic codons are underlined) arc annealed to the ssDNA uracil-containing template as follows: 5 μL of ssDNA template was added to 1 μL of 10 x annealing buffer (100 mM Tris-HCl, pH 8.0, 500 mM NaCl, 100 mM $MgCl_2$, 10 mM DTT), and 5 pmoles of oligonucleotide, adjusting the final volume to 10 µL with sterile water. The reaction mixture is incubated at 55° C. for 5 minutes, then cooled slowly to room temperature over 10 minutes. A mixture (4 µL) of all four deoxyribonucleotide triphosphates (2.5 mM of each) are added to the annealing reaction, along with 1 µL of 10x ligase buffer (660 mM Tris-HCl, pH 7.5, 50 mM MgCl$_2$, 50 mM DTT) and 1 µL of 10 mM rATP. To initiate the reaction, 2.5 units of E. coli DNA polymerase (Klenow fragment), 2.5 units of T4 DNA ligase and sterile water is added to give a final volume of 20 µL. After incubation at room temperature for 2 hours. additional DNA polymerase and DNA ligase are added (amounts as indicated above) and the mixture is incubated for an additional 2 hours. The reaction mixture (5 µL) is then transformed into E. coli strain JM101 and grown overnight on ampicillin-containing LB media plates. Ampicillin-resistant colonies from the fresh transformation plate are used to prepare ssDNA template (as described above) for screening for mutations by ssDNA sequencing. Mutant single-stranded DNA, identified through DNA sequencing, is retransformed into E. coli strain JM101 to prepare plasimid stocks for future use. Double-stranded DNA is prepared using the Qiagen DNA purification kits, according to the plasmid midi protocol provided with the Qiagen-tip 100.

Myoglobin is expressed in E. coli strain LF392 and is recovered and purified according to the procedure described in Example 2.

TABLE 3

| Mutations | Sequence |
| --- | --- |
| Lys45Glu | 5'-CAG GTG TTT GAA TTC ATC GAA TTT-'(SEQ ID. NO.9) |
| Lys63Glu | 5'-C AAC GGT ACC ATG TTC TTT CAG ATC TTC AG-3'(SEQ ID. NO:10) |

EXAMPLE 5

Mb variants containing Lys 45 Glu and Lys 45 Glu/Lys 63 Glu produced according to the methods of the proceeding example were characterized according to their Mu binding characteristics, peroxidase activity and Mn specific peroxidase activity. Table 1 shows the Mn peroxidase activity of the variants as compared to wild type Mb as determined in to the reaction described in Example 1. The variants have substitutions at both residues 45 and 63 showed greater Mn(II) peroxidase activity.

Binding of divalent metal ions to the Mb variants was measured by monitoring the release of protons upon binding of metal ions in solution to the protein. Standardized MnCl$_2$ (9988-2 E. Merck, N.J.) solutions are diluted gravimetrically to 3.8–5.2 mM and KCl is added to give a final ionic strength of 17.2 or 100 mM . The diluted metal ion solution and the Mb solution (30–40 µM in 17.2 mM or 100 mMKCl) are initially adjusted to the same pH. The protein solution is then titrated with metal ion, and the amount of metal bound by the protein is quantified through measuring the release of protons by titrating back to the original pH with 0.2 mM standardized NaOH. The initial pH of the titrations varies from pH5.5 to pH7.0. The digitized titration curves are fitted to equations for either a one site or two site model using Scientist (MicroMath, Inc.) and the binding constants ($K_1$ and $K_2$) and the stoichiometric number of protons released per mole of metal ion bound (q) are calculated. One and two site model equations are found in Mauk, M. R. et al (1991) "Proton Linkage of Complex Formation Between Cytochrome c and Cytochrome b$_3$: Electrostatic Consequences of Protein-Protein Inteructions", *Biochemistry* 39:9873–9881; and, Mauk, M. R. et al. (1994) "Proton Linkage in Formation of The Cytochrome c-Cytochrome c Peroxidase Complex: Electrostatic Properties of the High- and Low-Affinity Chytochrome Binding Sites on the Peroxidase", *Biochemistry* 33(42:) 12609–12614.

Although the wild-type protein exhibits one binding site with relatively low affinity, the variants exhibit an additional site that has a significant affinity for Mn(II) ions. Some representative association constants for interaction of Mn(II) with the myoglobin variants obtained at pH 7, 25° C. and an ionic strength of 0.017M KCl are shown in Table 4.

TABLE 4

| Protein | High-Affinity Site $K_1(M^{-1})$ | Low-Affinity Site $K_2(M^{-1})$ |
| --- | --- | --- |
| wild-type Mb | — | 690 ± 20 |
| K45E | 16,000 ± 1000 | 360 ± 10 |
| K45E/K63E | 12,800 ± 400 | 620 ± 20 |
| H97L/K45E/K63E/S92A | 14,800 ± 600 | 720 ± 30 |

Both binding sites show a strong pH dependence, decreasing in strength as the pH is lowered. Also, metal binding is decreased at higher ionic strengths. At low pH and high ionic strength, binding at the weak pro-existing site is not detected.

Competition EPR procedures using the Lys45Glu/Lys63Glu variant demonstrate relative affinities of different metal ions including Cu(II), Cu(II) and Cd(II). The approximate binding strengths of these metal ions to this variant is Mn(II)≈Cu(II)<Co(II)<Cd(II). Analysis of the crystal structure of the Lys45Glu/Lys63Glu Mb variant identifies only the heme propionate −6 and 45 Glu as provided direct ligands for metal binding but the additional negative charge at 63 Glu appears to provide for greater Mn peroxidase performance and/or Mn binding.

Various changes and modifications may be made in the practice of the invention disclosed and claimed herein without departing from the spirit and scope thereof.

We claim:

1. A method of catalysing a reaction with myoglobin in which a substrate is oxidized with a peroxide wherein, a reaction mixture is provided comprising substrate, peroxide and myoglobin, characterized in that the myoglobin has peroxidase activity greater than wild-type and a modified amino acid sequence in which one or more of the following amino acids are substituted: Thr 39, Lys/Arg 45, Phe 46, His 97 and He 107.

2. The method of claim 1 wherein one or more of Thr 39, Phe 46 and He 107 are substituted with an amino acid selected from the group consisting of: Leu, Ile, Val, Ala, Met, Phe and Gly.

3. The method of claim 2 wherein Lys/Arg 45 is substitued with Asp or Glu.

4. The method of claim 1 wherein the myoglobin has the following substitutions: Thr 39 Ile, Lys/Arg 45 Glu, Phe 46 Leu, and Ile 107 Phe.

5. The method of claim 4 wherein the myoglobin is additionally substituted at Lys 63 by Glu or Asp.

6. The method of claim 1 wherein Lys/Arg 45 and Lys 63 are substituted by Glu, and His 97 is substituted by Leu.

7. A method of catalysing oxidation of Mn(II) by hydrogen peroxide with myoglobin comprising:

(a) mixing Mn(II) substrate, hydrogen peroxide and myoglobin to provide a reaction mixture, and (b) maintaining the reaction mixture under conditions appropriate for oxidation of Mn(II) to be catalysed by myoglobin.

8. The method of claim 7 wherein the reaction mixture additionally comprises an organic chelator of Mn(III).

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 113 amino acids
        (B) TYPE: amino acid
        (C) STRANDEDNESS:
        (D) TOPOLOGY: linear (xi) SEQUENCE DESCRIPTION: SEQ ID NO:1:

```
Gly Leu Ser Asp Gly Glu Trp Gln Gln Val Leu Asn Val Trp Gly Lys
 1               5                  10                  15
Val Glu Ala Asp Ile Ala Gly His Gly Gln Glu Val Leu Ile Arg Leu
                20                  25                  30
Phe Thr Gly His Pro Glu Thr Leu Glu Lys Phe Asp Lys Phe Lys His
                35                  40                  45
Leu Lys Thr Glu Ala Glu Met Lys Ala Ser Glu Asp Leu Lys Lys His
        50                  55                  60
Gly Thr Val Val Leu Thr Ala Leu Gly Gly Ile Leu Lys Lys Lys Gly
 65                 70                  75                  80
His His Glu Ala Glu Leu Lys Pro Leu Ala Gln Ser His Ala Thr Lys
                85                  90                  95
His Lys Ile Pro Ile Lys Tyr Leu Glu Phe Ile Ser Asp Ala Ile Ile
               100                 105                 110
His
```

(2) INFORMATION FOR SEQ ID NO:2:

(i) SEQUENCE CHARACTERISTICS:
        (A) LENGTH: 113 amino acids
        (B) TYPE: amino acid
        (C) STRANDEDNESS:
        (D) TOPOLOGY: linear (xi) SEQUENCE DESCRIPTION: SEQ ID NO:2:

```
Val Leu Ser Glu Gly Glu Trp Gln Leu Val Leu His Val Trp Ala Lys
 1               5                  10                  15
Val Glu Ala Asp Val Ala Gly His Gly Gln Asp Ile Leu Ile Arg Leu
                20                  25                  30
Phe Lys Ser His Pro Glu Thr Leu Glu Lys Phe Asp Arg Phe Lys His
                35                  40                  45
Leu Lys Thr Glu Ala Glu Met Lys Ala Ser Glu Asp Leu Lys Lys His
        50                  55                  60
Gly Val Thr Val Leu Thr Ala Leu Gly Ala Ile Leu Lys Lys Lys Gly
 65                 70                  75                  80
His His Glu Ala Glu Leu Lys Pro Leu Ala Gln Ser His Ala Thr Lys
                85                  90                  95
His Lys Ile Pro Ile Lys Tyr Leu Glu Phe Ile Ser Glu Ala Ile Ile
               100                 105                 110
His
```

(2) INFORMATION FOR SEQ ID NO:3:

(i) SEQUENCE CHARACTERISTICS:
        (A) LENGTH: 113 amino acids (B) TYPE: amino acid
(C) STRANDEDNESS:
(D) TOPOLOGY: linear (xi) SEQUENCE DESCRIPTION: SEQ ID NO:3:

```
Gly Leu Ser Asp Gly Glu Trp Gln Ala Val Leu Asn Ala Trp Gly Lys
  1               5                  10                  15
Val Glu Ala Asp Val Ala Gly His Gly Gln Glu Val Leu Ile Arg Leu
             20                  25                  30
Phe Thr Gly His Pro Glu Thr Leu Glu Lys Phe Asp Lys Phe Lys His
         35                  40                  45
Leu Lys Thr Glu Ala Glu Met Lys Ala Ser Glu Asp Leu Lys Lys His
     50                  55                  60
Gly Asn Thr Val Leu Thr Ala Leu Gly Gly Ile Leu Lys Lys Lys Gly
 65                  70                  75                  80
His His Glu Ala Glu Val Lys His Leu Ala Glu Ser His Ala Asn Lys
                 85                  90                  95
His Lys Val Pro Ile Lys Tyr Leu Glu Phe Ile Ser Asp Ala Ile Ile
            100                 105                 110
His
```

(2) INFORMATION FOR SEQ ID NO:4:

(i) SEQUENCE CHARACTERISTICS:
    (A) LENGTH: 113 amino acids
    (B) TYPE: amino acid
    (C) STRANDEDNESS:
    (D) TOPOLOGY: linear (xi) SEQUENCE DESCRIPTION: SEQ ID NO:4:

```
Gly Leu Ser Asp Gly Glu Trp Gln Leu Val Leu Asn Ala Trp Gly Lys
  1               5                  10                  15
Val Glu Ala Asp Val Ala Gly His Gly Gln Glu Val Leu Ile Arg Ile
             20                  25                  30
Phe Thr Gly His Pro Glu Thr Leu Glu Lys Phe Asp Lys Phe Lys His
         35                  40                  45
Leu Lys Thr Glu Ala Glu Met Lys Ala Ser Glu Asp Leu Lys Lys His
     50                  55                  60
Gly Asn Thr Val Leu Thr Ala Leu Gly Gly Ile Leu Lys Lys Lys Gly
 65                  70                  75                  80
His His Glu Ala Glu Val Lys His Ile Ala Glu Ser His Ala Asn Lys
                 85                  90                  95
His Lys Ile Pro Val Lys Tyr Leu Glu Phe Ile Ser Asp Ala Ile Ile
            100                 105                 110
His
```

(2) INFORMATION FOR SEQ ID NO:5:

(i) SEQUENCE CHARACTERISTICS:
    (A) LENGTH: 113 amino acids
    (B) TYPE: amino acid
    (C) STRANDEDNESS:
    (D) TOPOLOGY: linear (xi) SEQUENCE DESCRIPTION: SEQ ID NO:5:

```
Gly Leu Ser Asp Gly Glu Trp Gln Leu Val Leu Asn Val Trp Gly Lys
  1               5                  10                  15
Val Glu Ala Asp Ile Pro Gly His Gly Gln Glu Val Leu Ile Arg Leu
             20                  25                  30
```

```
        Phe  Lys  Gly  His  Pro  Glu  Thr  Leu  Glu  Lys  Phe  Asp  Lys  Phe  Lys  His
                  35                      40                      45

Leu  Lys  Ser  Glu  Asp  Glu  Met  Lys  Ala  Ser  Glu  Asp  Leu  Lys  Lys  His
             50                      55                      60

Gly  Ala  Thr  Val  Leu  Thr  Ala  Leu  Gly  Gly  Ile  Leu  Lys  Lys  Lys  Gly
        65                           70                      75                      80

His  His  Glu  Ala  Glu  Ile  Lys  Pro  Leu  Ala  Gln  Ser  His  Ala  Thr  Lys
                            85                      90                      95

His  Lys  Ile  Pro  Val  Lys  Tyr  Leu  Glu  Phe  Ile  Ser  Glu  Cys  Ile  Ile
                       100                     105                     110

Gln
```

( 2 ) INFORMATION FOR SEQ ID NO:6:

( i ) SEQUENCE CHARACTERISTICS:
        ( A ) LENGTH: 532 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:6:

```
GATCCATAAC  TAACTAATCT  AGAAATAATT  TTGTTTAACT  TTAAGAAGGA  GATATATCCA    60
TGGGTCTGTC  TGATGGTGAA  TGGCAGCAGG  TTCTGAACGT  TTGGGGCAAA  GTTGAAGCTG   120
ACATCGCTGG  TCACGGTCAA  GAAGTCTTGA  TTCGACTGTT  CACCGGCCAC  CCGGAAACTC   180
TGGAAAAATT  CGATAAATTC  AAACACCTGA  AAACTGAAGC  TGAAATGAAG  GCGTCTGAAG   240
ATCTGAAAAA  ACATGGTACC  GTTGTGTTAA  CTGCCCTAGG  TGGCATCCTT  AAGAAAAAAG   300
GGCACCACGA  AGCTGAGCTC  AAACCGCTTG  CGCAATCGCA  TGCTACTAAA  CACAAGATCC   360
CGATCAAATA  CCTGGAATTC  ATCTCTGATG  CGATCATCCA  CGTTCTGCAT  TCTAAACATC   420
CAGGTGACTT  CGGTGCTGAC  GCTCAGGGTG  CTATGACCAA  AGCTCTCGAG  CTGTTCCGTA   480
ACGATATCGC  TGCTAAGTAC  AAAGAACTGG  GTTTCCAGGG  TTAATGACTG  CA           532
```

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
TGTAAAACGA  CGGCCAGT                                                      18
```

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
CAGGAAACAG  CTATGACC                                                      18
```

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

CAGGTGTTTG AATTCATCGA ATTT 24

( 2 ) INFORMATION FOR SEQ ID NO:10:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:10:

CAACGGTACC ATGTTCTTTC AGATCTTCAG 30

( 2 ) INFORMATION FOR SEQ ID NO:11:

( i ) SEQUENCE CHARACTERISTICS:
( A ) LENGTH: 154 amino acids
( B ) TYPE: amino acid
( C ) STRANDEDNESS:
( D ) TOPOLOGY: linear ( x i ) SEQUENCE DESCRIPTION: SEQ ID NO:11:

| Met | Gly | Leu | Ser | Asp | Gly | Glu | Trp | Gln | Gln | Val | Leu | Asn | Val | Trp | Gly |
|---|---|---|---|---|---|---|---|---|---|---|---|---|---|---|---|
| 1 | | | | 5 | | | | | 10 | | | | | 15 | |
| Lys | Val | Glu | Ala | Asp | Ile | Ala | Gly | His | Gly | Gln | Glu | Val | Leu | Ile | Arg |
| | | | 20 | | | | | 25 | | | | | 30 | | |
| Leu | Phe | Thr | Gly | His | Pro | Glu | Thr | Leu | Glu | Lys | Phe | Asp | Lys | Phe | Lys |
| | | 35 | | | | | 40 | | | | | 45 | | | |
| His | Leu | Lys | Thr | Glu | Ala | Glu | Met | Lys | Ala | Ser | Glu | Asp | Leu | Lys | Lys |
| | 50 | | | | | 55 | | | | | 60 | | | | |
| His | Gly | Thr | Val | Val | Leu | Thr | Ala | Leu | Gly | Gly | Ile | Leu | Lys | Lys | Lys |
| 65 | | | | | 70 | | | | | 75 | | | | | 80 |
| Gly | His | His | Glu | Ala | Glu | Leu | Lys | Pro | Leu | Ala | Gln | Ser | His | Ala | Thr |
| | | | | 85 | | | | | 90 | | | | | 95 | |
| Lys | His | Lys | Ile | Pro | Ile | Lys | Tyr | Leu | Glu | Phe | Ile | Ser | Asp | Ala | Ile |
| | | | 100 | | | | | 105 | | | | | 110 | | |
| Ile | His | Val | Leu | His | Ser | Lys | His | Pro | Gly | Asp | Phe | Gly | Ala | Asp | Ala |
| | | 115 | | | | | 120 | | | | | 125 | | | |
| Gln | Gly | Ala | Met | Thr | Lys | Ala | Leu | Glu | Leu | Phe | Arg | Asn | Asp | Ile | Ala |
| | 130 | | | | | 135 | | | | | 140 | | | | |
| Ala | Lys | Tyr | Lys | Glu | Leu | Gly | Phe | Gln | Gly |
| 145 | | | | | 150 | | | | |